(12) United States Patent
Kwon et al.

(10) Patent No.: US 10,660,655 B2
(45) Date of Patent: May 26, 2020

(54) MEDICAL DRILL DEVICE

(71) Applicant: KOH YOUNG TECHNOLOGY INC., Seoul (KR)

(72) Inventors: Young Sik Kwon, Ansan-si (KR); Seung Chul Han, Asan-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 354 days.

(21) Appl. No.: 15/325,478

(22) PCT Filed: Jul. 13, 2015

(86) PCT No.: PCT/KR2015/007260
§ 371 (c)(1),
(2) Date: Jan. 11, 2017

(87) PCT Pub. No.: WO2016/006983
PCT Pub. Date: Jan. 14, 2016

(65) Prior Publication Data
US 2017/0150973 A1    Jun. 1, 2017

(30) Foreign Application Priority Data

Jul. 11, 2014 (KR) .................. 10-2014-0087474
Jul. 13, 2015 (KR) .................. 10-2015-0099061

(51) Int. Cl.
*A61B 17/16*    (2006.01)
*A61B 17/17*    (2006.01)
(Continued)

(52) U.S. Cl.
CPC .......... *A61B 17/16* (2013.01); *A61B 17/1695* (2013.01); *A61B 17/17* (2013.01);
(Continued)

(58) Field of Classification Search
CPC . A61B 17/1666; A61B 17/17; A61B 17/1739; A61B 17/16; A61B 17/1695;
(Continued)

(56) References Cited

U.S. PATENT DOCUMENTS 3,838,517 A * 10/1974 Michnick ............... A61C 1/082
433/72
5,207,681 A * 5/1993 Ghadjar ............. A61B 17/1695
606/180

(Continued)

FOREIGN PATENT DOCUMENTS

CN    2010-79422    7/2008
CN    201356602    12/2009
(Continued)

OTHER PUBLICATIONS

International Search Report for International Application No. PCT/KR2015/007260, dated Aug. 20, 2015.
(Continued)

*Primary Examiner* — Matthew J Lawson
(74) *Attorney, Agent, or Firm* — Kile Park Reed & Houtteman PLLC

(57) ABSTRACT

The present invention relates to a medical drill device. The medical drill device includes a boring drill including a motor and a drill part; an instrument body coupled to the boring drill; and a plurality of supporting rods coupled to the instrument body so as to support the boring drill to a work area. Each of the supporting rods includes: a straight portion inserted into the corresponding supporting rod insertable part in such a manner that the supporting rod is linearly moved with the instrument body; and a bent portion bent at a predetermined angle from the straight portion. As such, by using the supporting rods having a bent structure to support a boring drill to a work area and simultaneously limiting a
(Continued)

boring depth of the boring drill, it is possible to shorten boring time and ensure safety of the boring operation.

8 Claims, 4 Drawing Sheets

(51) Int. Cl.
  *A61B 17/32* (2006.01)
  *A61B 90/00* (2016.01)
(52) U.S. Cl.
  CPC ............. *A61B 2017/320052* (2013.01); *A61B 2090/034* (2016.02); *A61B 2090/036* (2016.02)
(58) Field of Classification Search
  CPC .... A61B 17/7055; A61B 2017/320052; A61B 8/0808; A61B 2090/034; A61B 2090/036
  USPC .......................................................... 606/80
  See application file for complete search history.

(56) References Cited

U.S. PATENT DOCUMENTS

| | | | |
|---|---|---|---|
| 5,575,794 A | 11/1996 | Walus et al. | |
| 5,827,288 A * | 10/1998 | Umber | A61B 17/1695 606/80 |
| 6,395,005 B1 | 5/2002 | Lovell | |
| 9,022,949 B2 | 5/2015 | Herndon | |
| 2007/0118135 A1 | 5/2007 | Mansmann | |
| 2008/0221581 A1* | 9/2008 | Shoham | A61B 17/17 606/96 |
| 2009/0228031 A1* | 9/2009 | Ritter | A61B 17/1635 606/167 |
| 2010/0082035 A1 | 4/2010 | Keefer | |
| 2010/0311006 A1* | 12/2010 | Lancieux | A61C 1/084 433/75 |
| 2010/0312244 A1* | 12/2010 | Edwards | A61B 17/1725 606/62 |
| 2011/0190789 A1* | 8/2011 | Thiran | A61B 17/1739 606/130 |
| 2011/0208196 A1 | 8/2011 | Radermacher et al. | |
| 2011/0245833 A1* | 10/2011 | Anderson | A61B 17/1626 606/80 |
| 2013/0096574 A1* | 4/2013 | Kang | A61B 17/1622 606/130 |
| 2013/0172898 A1* | 7/2013 | Iannotti | A61B 17/1739 606/102 |
| 2013/0204254 A1* | 8/2013 | Slone | A61B 17/1666 606/81 |
| 2014/0239600 A1* | 8/2014 | Walsh | B23B 41/00 279/141 |
| 2015/0066030 A1* | 3/2015 | McGinley | A61B 17/16 606/79 |
| 2015/0182285 A1* | 7/2015 | Yen | G05B 15/02 606/80 |
| 2015/0190151 A1* | 7/2015 | Budhabhatti | A61B 17/1666 606/96 |

FOREIGN PATENT DOCUMENTS

| | | |
|---|---|---|
| KR | 10-1005952 | 1/2011 |
| WO | 2013/152102 | 10/2013 |

OTHER PUBLICATIONS

Chinese Office Action with English translation for Chinese Application No. 201580037634, dated Jul. 25, 2018.
Chinese Office Action with English translation for Chinese Application or Patent No. 201580037634.7, dated Jan. 17, 2019.
Chinese Office Action with English translation corresponding to Chinese Application No. or Publication No. 201580037634.7, dated Jul. 22, 2019.

* cited by examiner

MEDICAL DRILL DEVICE

TECHNICAL FIELD

The present invention relates to a medical drill device and more particularly, to a medical drill device capable of ensuring accuracy and stability of a boring operation in boring a bone of a specific portion into a circular shape having a certain size.

The present invention has been derived from a research undertaken as part of the industrial source technology development business of the Ministry of Knowledge Economy.

[Assignment Identification Number: 10040097, Research Project: Development of technology of minimal invasive multi-degree of freedom surgical robot system for medical surgical robot image-based otolaryngology and neurosurgery]

BACKGROUND

In the medical surgical fields including stereotactic surgery such as deep brain stimulation (DBS) and the like, a process of boring a bone of a specific portion in a certain size is required to insert a surgical tool, such as a micro-electrode or the like, into the human body.

In general, an operation of boring a bone for surgery is conducted manually by an operator using a surgical drill device while checking a boring portion directly with the naked eyes.

However, performing such a manual bone boring operation based on the operator's senses has resulted in degradation in the accuracy of the boring operation depending on the skill level of the operator and in requiring a substantial amount of time for such boring operation. Further, it may be difficult in such operation to bore a bone of an exact diameter and depth intended by the operator.

SUMMARY

In consideration of above problems, the present invention provides embodiments of a medical drill device which is capable of increasing the boring accuracy and shortening boring time by combining a typical boring drill and an assistant tool.

According to one embodiment of the present invention, a medical drill device includes: a boring drill including a motor and a drill part which is configured to bore a portion of a bone based on a torque of the motor; an instrument body coupled to surround a portion of the boring drill; and a plurality of supporting rods coupled to the instrument body so as to support the boring drill to a work area.

The instrument body may include supporting rod insertable parts, in each of which a portion of a corresponding one of the supporting rods is inserted, and the supporting rods may be coupled to the respective supporting rod insertable parts such that the supporting rods are capable of moving linearly relative to the instrument body.

Each of the supporting rods may include: a straight portion inserted into the corresponding supporting rod insertable part such that the supporting rod is capable of moving linearly with respect to the instrument body; and a bent portion bent at a predetermined angle from the straight portion for limiting linear motion of the instrument body.

The medical drill device may further include a depth setting part which limits linear motion of the supporting rod.

The depth setting part may be installed in the opposite side of the supporting rod with respect to the instrument body and set a boring depth through adjustment of a distance between the depth setting part and the supporting rod.

The straight portion may include a depth indicator formed on an outer surface of the straight portion for indicating a boring depth.

The medical drill device may further include an elastic member formed in the supporting rod insertable parts to return to an original position according to an elastic force after a linear motion of the instrument body.

The medical drill device may further include at least one stopper coupled to protrude by a predetermined height from the instrument body for limiting movement of the boring drill.

The plurality of supporting rods may be formed at a regular interval along a circumferential direction of the instrument body, and the stoppers may be formed at a predetermined interval between the supporting rods along the circumferential direction of the instrument body.

With the above-described medical drill device, it is possible to shorten boring time and ensure safety of the boring operation by using supporting rods having a bent structure to support a boring drill to a work area and simultaneously limiting a boring depth of the boring drill.

In addition, by additionally installing a stopper as a secondary safeguard in addition to a supporting rod as the primary safeguard, it is possible to further improve the safety of the boring operation.

DETAILED DESCRIPTION

Figure 1:
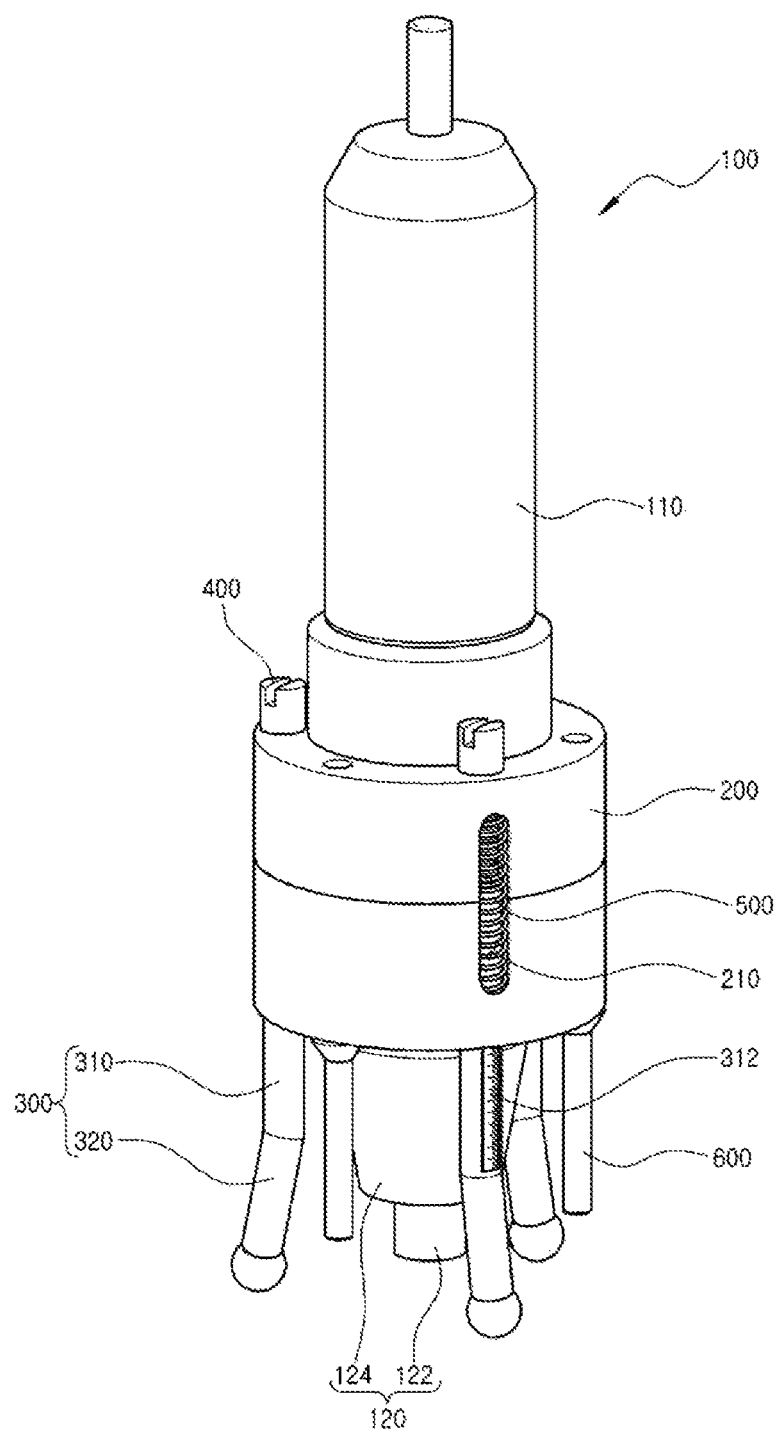
FIG. 1 is a perspective view illustrating a medical drill device according to one embodiment of the present invention.

The present invention may be modified in various ways and have different forms. Some exemplary embodiments of the present invention are illustrated in the drawings and will be described below in detail. However, these embodiments are not intended to limit the present invention to the disclosed specific forms, but it is to be understood that the present invention covers all modifications, equivalents and substitutes included in the spirit and scope of the present invention.

The terms "first," "second" and the like used herein may be used to describe various elements, but the elements shall not be restricted by these terms. These terms are only used to distinguish one element from the other. For example, a first element may be termed a second element and vice versa without departing from the scope of the present invention.

The terms used herein are merely used to describe particular embodiments, but are not intended to limit the present invention. Expression in the singular includes a plural form unless explicitly stated otherwise. In this application, the terms "comprise," "include," "have" or the like used herein are intended to indicate the existence of features, numbers, steps, operations, elements, parts or combinations thereof described in the specification, but are not intended to exclude the existence or addition of one or more of other features, numbers, steps, operations, elements, parts or combinations thereof.

Unless otherwise defined, all terms used herein, including technical and scientific terms, have the same meanings as commonly understood by those skilled in the art.

General terms defined in dictionaries shall be construed to have the same meanings in the context of the relevant art, but, unless explicitly defined otherwise, shall not be construed to have idealistically or excessively formalistic meanings.

Preferred embodiments of the present invention will now be described in more detail with reference to the accompanying drawings.

Figure 2:
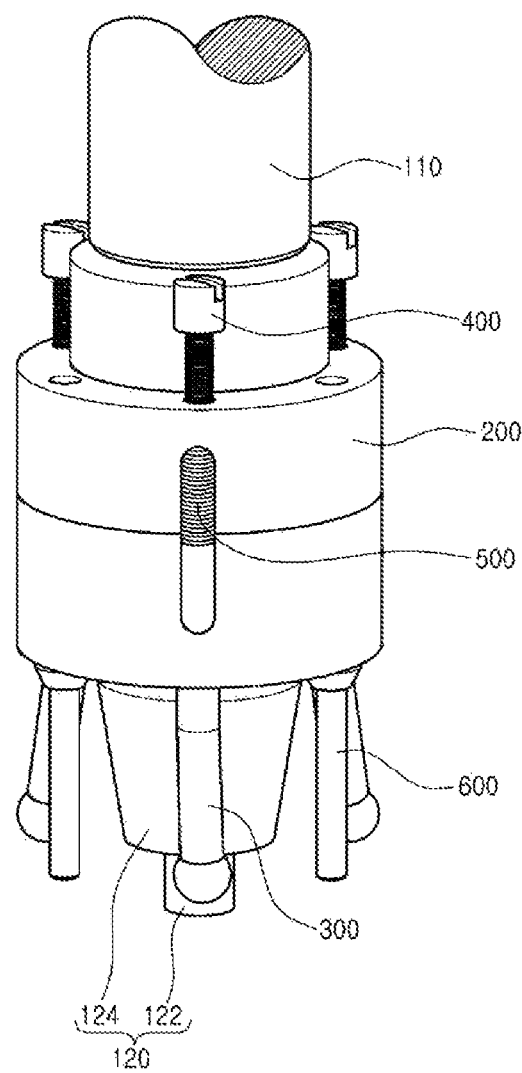
FIG. 2 is a partially-enlarged view illustrating an instrument body portion in detail.

FIG. 1 a perspective illustrating a medical drill device according to one embodiment of the present invention. FIG. 2 is a partially-enlarged view illustrating an instrument body portion in detail.

Referring to FIGS. 1 and 2, a medical drill device according to one embodiment of the present invention includes a boring drill 100 an instrument body 200 coupled to the boring drill 100, and a plurality of supporting rods 300 coupled to the instrument body 200 so as to support the boring drill 100 to a work area.

The boring drill 100 includes a motor 110 to generate a torque and a drill part 120 for boring a portion of a bone through the torque of the motor 110.

The drill part 120 includes a drill bit 122 which is connected to the motor 110 and rotates according to rotation of the motor 110, and a drill chuck 124 which is coupled to the instrument body 200 and covers the drill bit 122 such that a portion of the drill bit 122 is exposed. The drill bit 122 may be used in a variety of sizes according to an intended boring diameter. For example, the drill bit 122 is formed in a diameter of about 10 mm. The drill bit 122 and the drill chuck 124 may be integrated in a form which can be attached to or detached from the instrument body 200.

The instrument body 200 is coupled to the boring drill 100 so as to surround a portion of the boring drill 100. For example, if the boring drill 100 is formed in a cylindrical shape, the instrument body 200 is formed in a cylindrical shape corresponding to the boring drill 100 and has a structure in which a cylindrical through-hole is formed such that the boring drill 100 can be inserted and fixed inside the instrument body 200.

The instrument body 200 includes a plurality of supporting rod insertable parts 210, into each of which a portion of a corresponding one of the supporting rods 300 is inserted. For example, the supporting rod insertable parts 210 are formed in a shape of a hole which penetrates from the bottom to the top of the instrument body 200. The plurality of supporting rod insertable parts 210 is formed at a regular interval along a circumferential direction of the instrument body 200 corresponding to installation positions of the supporting rods 300.

The supporting rods 300 are coupled to a lower portion of the instrument body 200 so as to support the boring drill 100 to a work area for boring. For example, the supporting rods 300 are respectively coupled to the supporting rod insertable parts 210 so as to ensure a rectilinear reciprocating movement with respect to the instrument body 200.

More specifically, each of the supporting rods 300 includes a straight portion 310 which is inserted into the respective supporting rod insertable part 210 so as to ensure a rectilinear reciprocating movement with respect to the instrument body 200, and a bent portion 320 bent at a predetermined angle from the straight portion 310 so as to limit the linear motion of the instrument body 200. During boring, the boring drill 100 and the instrument body 200 coupled to the boring drill 100 perform a boring operation while descending along the straight portions 310 of the supporting rods 300. At this time, further descent is limited by the bent portions 320 so that a boring depth is limited to prevent the boring operation from being performed beyond an intended depth. Thus, the supporting rods 300 function as a safeguard to prevent the boring operation from being performed beyond the intended depth while supporting the boring drill 100 to the work area.

The medical drill device of the present invention may further include depth setting parts 400 for setting a boring depth. The depth setting parts 400 can limit the linear motion of the supporting rods 300 for setting of the boring depth for the boring drill 100. For example, the depth setting parts 400 are installed in the opposite side of the supporting rods 300 with respect to the instrument body 200 and may set the boring depth by adjusting a distance by which the supporting rods 300 are inserted into the supporting rod insertable parts 210.

In one embodiment, a portion of each of the depth setting parts 400 is exposed to the top of the instrument body 200, while the remaining portion of each of the depth setting parts 400 is placed within each of the corresponding supporting rod insertable parts 210 of the instrument body 200. At this time, the depth setting parts 400 and the corresponding supporting rod insertable parts 210 are coupled to each other by a screw connecting method and a distance between the depth setting parts 400 and the supporting rods 300 can be adjusted through the screwing of the depth setting parts 400. In addition to the screw connecting method, other various methods for setting the boring depth may be used to adjust the relative distance between the depth setting parts 400 and the supporting rods 300.

In the meantime, in setting the boring depth by means of the depth setting parts 400, a depth indicator 312 may be formed on the outer surface of each of the straight portions 310 of the supporting rods 300 in order to indicate the intended boring depth. Thus, an operator can set the intended boring depth through the depth setting parts 400 while observing a scale marking of the depth indicators 312. In addition to the outer surface of the straight portions 310, the depth indicators 312 may be formed around the instrument body 200, the supporting rod insertable parts 210, or the like, to indicate a boring depth.

The medical drill device of the present invention may further include an elastic member 500 which is formed in the supporting rod insertable parts 210 in order to return the instrument body 200 to its original position by an elastic force after a linear motion of the instrument body 200. That is, upon completion of a boring operation through the descending motion of the boring drill 100 and the instrument body 200, the boring drill 100 and the instrument body 200 move up to return to their original position by the elastic force of the elastic member 500. The elastic member 500 is formed of, for example, a spring which is inserted into the supporting rod insertable parts 210.

The medical drill device of the present invention may further include at least one stopper 600 to prevent the boring drill 100 from penetrating beyond the intended depth. The stopper 600 is coupled to the instrument body 200 so as to protrude by a predetermined height from the instrument body 200 in order to limit the movement of the boring drill 100. For example, a plurality of stoppers 600 is formed at a predetermined interval between the supporting rods 300 along a circumferential direction of the instrument body 200.

In this manner, when the boring drill 100 and the instrument body 200 descend for boring, in addition to the primary safeguard, i.e., the bent portions 320 of the supporting rods 300, the secondary safeguard, i.e., the stopper 600, is additionally installed, thereby further improving the safety of the boring operation.

Figure 3:
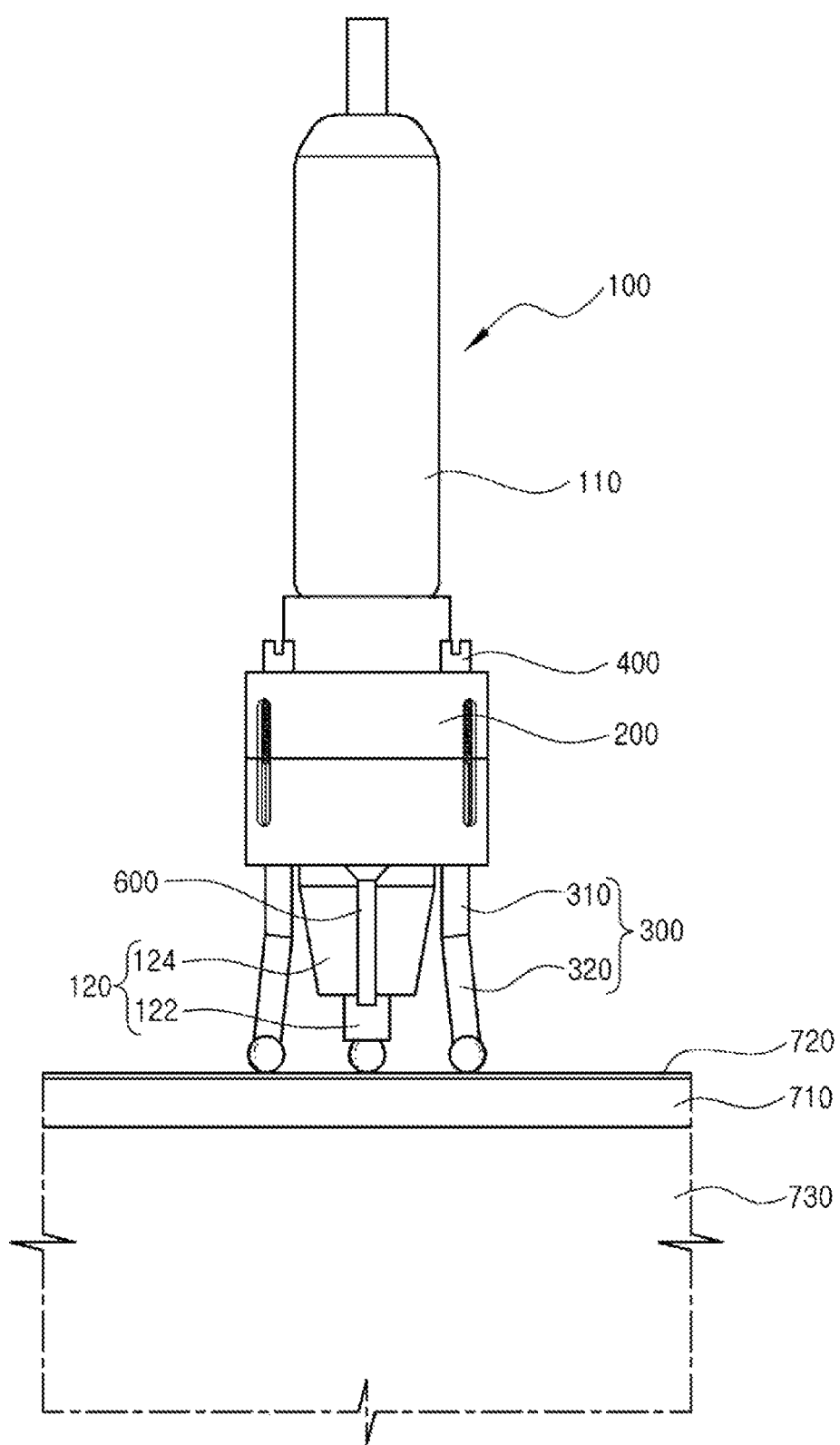
FIG. 3 is a view illustrating a state of installation of a medical drill device before a boring operation according to one embodiment of the present invention.
Figure 4:
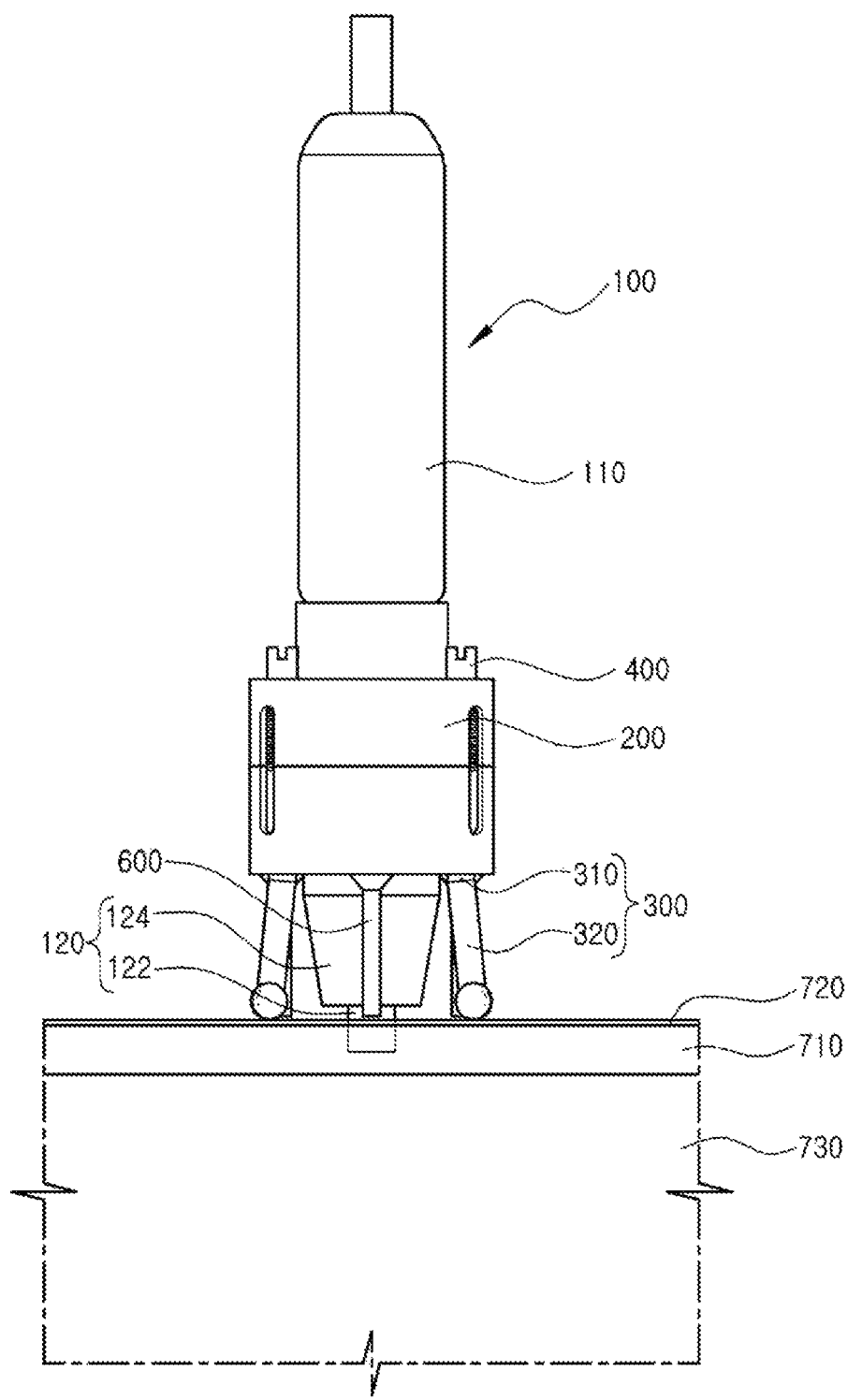
FIG. 4 is a view illustrating a state of installation of a medical drill device during a boring operation according to one embodiment of present invention.

FIG. 3 is a view illustrating a state of installation of the medical drill device before a boring operation according to one embodiment of the present invention. FIG. 4 is a view illustrating a state of installation of the medical drill device in a boring operation according to one embodiment of the present invention. In FIGS. 3 and 4, reference numerals 710, 720, and 730 denote a bone, a skin, and an internal organ, respectively.

Referring to FIGS. 1 and 3, prior to boring the bone 710 in a certain portion, a boring depth intended for the medical drill device is set. For example, the boring depth is set to correspond to the thickness of the bone 710 through manipulation of the depth setting parts 400. In setting the boring depth, the operator can precisely set the intended boring depth by referring to the depth indicators 312 formed on the straight portions 310 of the supporting rods 300.

After setting the boring depth by means of the depth setting parts 400, the medical drill device is placed in a work area of a patient for boring so as to be supported by the supporting rods 300, as shown in FIG. 3. In this basic installation of the medical drill device, the drill bit 122 is located to be spaced apart by a predetermined distance from the skin 720 and the bone 710 and the lower end of the stopper 600 is located to be slightly lower than the bottom of the drill chuck 124.

Referring to FIGS. 1 and 4, in a state where the medical drill device is settled through the supporting rods 300, a boring operation for the bone 710 is performed as the boring drill 100 descends. When the boring drill 100 descends, the supporting rods 300 maintain their fixed positions, while the instrument body 200 together with the boring drill 100 descends along the straight portions 310 of the supporting rods 300.

On the other hand, the descending motion of the boring drill 100 and the instrument body 200 is limited by the bent portions 320 of the supporting rods 300. That is, when the instrument body 200 encounters the bent portions 320 of the supporting rods 300 while descending along the straight portions 310 of the supporting rods 300, the instrument body 200 is prevented from descending further and is stopped. In this manner, by using the supporting rods 300 having a bent structure to support the boring drill 100 to the work area and simultaneously limit the boring depth of the boring drill 100, it is possible to achieve the primary safety function of preventing the internal organ 730 from being damaged due to boring beyond the intended depth.

In addition, the descending motion of the boring drill 100 and the instrument body 200 can be limited by the stopper 600. That is, as the boring drill 100 and the instrument body 200 descend, if the stopper 600 coupled to the lower portion of the instrument body 200 contacts the patient's body, the boring drill 100 and the instrument body 200 can descend no further and are stopped. In this manner, by additionally installing the stopper 600 as a secondary safeguard in case the primary safety measure by the supporting rods 300 is insufficient, it is possible to further improve the safety of the boring operation.

On the other hand, after completion of the boring operation, when a force exerted on the boring drill 100 is removed, the boring drill 100 and the instrument body 200 move up to return to their original positions by the elastic force of the elastic member 500.

While certain embodiments have been described, these embodiments have been presented by way of example only, and are not intended to limit the scope of the disclosures. Indeed, the novel methods and apparatuses described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

EXPLANATION OF REFERENCE NUMERALS

100: boring drill,
110: motor,
120: drill part,
122: dill bit,
124: drill chuck,
200: instrument body,
210: supporting rod insertable part,
300: supporting rod,
310: straight portion,
312: depth indicator,
320: bent portion,
400: depth setting part,
500: elastic member,
600: stopper

What is claimed is:

1. A medical drill device comprising:
a boring drill including a motor and a drill part;
an instrument body coupled to the boring drill;
a plurality of supporting rods coupled to the instrument body and configured to support the instrument body and the boring drill over a work area; and
at least one stopper protruding from a lower portion of the instrument body towards the work area, configured to stop the instrument body and the boring drill from descending upon making a contact with the work area as the at least one stopper descends.

2. The medical drill device of claim 1, wherein the instrument body includes supporting rod insertable parts, in each of which a portion of a corresponding one of the supporting rods is inserted, and
wherein the supporting rods are coupled to the respective supporting rod insertable parts such that the supporting rods are capable of moving linearly relative to the instrument body.

3. The medical drill device of claim 2, wherein each of the supporting rods includes:
a straight portion inserted into one of the supporting rod insertable parts such that a corresponding supporting rod is capable of moving linearly with respect to the instrument body; and
a bent portion bent at a predetermined angle from the straight portion.

4. The medical drill device of claim 3, further comprising:
a depth setting part limiting a linear motion of one of the supporting rods.

5. The medical drill device of claim 4, wherein the depth setting part is installed in the opposite side of the supporting rods with respect to the instrument body and sets a boring depth through adjustment of a distance between the depth setting part and the one of the supporting rods.

6. The medical drill device of claim 5, wherein the straight portion includes a depth indicator formed on an outer surface of the straight portion.

7. The medical drill device of claim 2, further comprising:
an elastic member formed in one of the supporting rod insertable parts.

8. The medical drill device of claim 1, wherein the plurality of supporting rods is formed at a regular interval along a circumferential direction of the instrument body, and
wherein the at least one stopper is formed at a predetermined interval between the supporting rods along the circumferential direction of the instrument body.

* * * * *